(12) United States Patent
Chakravarti et al.

(10) Patent No.: US 8,557,527 B2
(45) Date of Patent: Oct. 15, 2013

(54) CORRELATION OF MOLECULAR MARKERS WITH CLINICAL OUTCOME IN GBM PATIENTS RADIATION TREATED WITH OR WITHOUT GEFITINIB

(75) Inventors: Arnab Chakravarti, Dublin, OH (US); Robert Pinard, Andover, MA (US); Donald Waldron, Fairfield, CT (US); Alpana Waldron, legal representative, Fairfield, CT (US); Agnes Ang, Newbury Park, CA (US); Marisa P. Dolled-Filhart, New Haven, CT (US); Annette Molinaro, New Haven, CT (US)

(73) Assignees: HistoRx, Inc., New Haven, CT (US); Radiation Therapy Oncology Group of the American College of Radiology, Philadelphia, PA (US)

( * ) Notice: Subject to any disclaimer, the term of this patent is extended or adjusted under 35 U.S.C. 154(b) by 88 days.

(21) Appl. No.: 12/564,698

(22) Filed: Sep. 22, 2009

(65) Prior Publication Data

US 2010/0144540 A1 Jun. 10, 2010

Related U.S. Application Data

(60) Provisional application No. 61/136,642, filed on Sep. 22, 2008.

(51) Int. Cl.
*G01N 33/53* (2006.01)
(52) U.S. Cl.
USPC .......................................................... 435/7.1
(58) Field of Classification Search
None
See application file for complete search history.

(56) References Cited

U.S. PATENT DOCUMENTS

2003/0045451 A1 3/2003 Bacus

OTHER PUBLICATIONS

Ali-Osman et al (Clinical Cancer Research, 1997, 12 Pt 1: 2253-2261).*
Osman et al (Clinical Cancer Research, 1997, 12 Pt 1: 2253-2261).*
Reyaz et al (J Col Physicians Surg Pak, 2005, 15(8): Abstract).*
McComb et al (Neurol Clin, 1985, 3(4): Abstract).*
Liang et al (BMC Cancer, 2006, 6(97): 1-16).*
Etienne et al (Clinical Cancer Research, 1998, 4: 2383-2390).*
Ermoian et al (Clin Cancer Res, 2002, 8(5): 1100-1106).*
Reyaz et al (J Col Physicians Surg Pak, 2005, 15(8): 472-475).*
McComb et al (Neurol Clin, 1985, 3(4): 711-728).*
Tockman et al (Cancer Res., 1992, 52:2711s-2718s).*
Franceschi et al (British Journal of Cancer, 2007, 96: 1047-1051).*
Pelloski et al (Clinical Cancer Research, 2006, 12: 3935-3941).*
Ochs et al (Int J Radiation Oncology Biol Phys, 2004, 58(3): 941-949).*
Stea et al (Cancer Lett, 2003, 202(1): 43-51).*
Mellinghoff et al (New England Journal of Medicine, 2005, 353: 2012-2024).*
Ermoian et al. "Dysregulation of PTEN and Protein Kinase B is Associated with Glioma Histology and Patient Survival" Clincial Cancer Research, May 1, 2002, vol. 8, No. 5, pp. 1100-1106.
International Search Report (PCT/US2009/057857) dated Apr. 7, 2010.
Jiang, et al "Phosphatase and Tensin Homologue Deficiency in Glioblastoma Confers Resistance to Radiation and Temozolomide that is Reversed by the Protease Inhibitor Nelfinavir" Cancer Research, May 9, 2007, vol. 67, No. 9, pp. 4467-4473.
Kanamori et al. "PTEN Expression is Associated with Prognosis for Patients with Advanced Endometrial Carcinoma Undergoing Post-operative Chemotherapy" International Journal of Cancer, Aug. 20, 2002, vol. 100, No. 6, pp. 686-689.
Sano et al. "Differential Expression of MMAC/PTEN in Glioblastoma Multiforme: Relationship to Localization and Prognosis" Cancer Research, Apr. 15, 1999, vol. 59, No. 8, pp. 1820-1824.
Terakawa et al. "Loss of PTEN expression followed by Akt phosphorylation is a poor prognostic factor for patients with endometrial cancer" Endocrine-Related Cancer, Jun. 2003, vol. 10, No. 2, pp. 203-208.
Wick, et al. "PTEN gene transfer in human malignant glioma: sensitization to irradiation and CD95L-induced apoptosis" Oncogene, Jul. 8, 1999, vol. 18, No. 27, pp. 3936-3943.
Haas-Kogan, D., et al., "Epidermal Growth Factor Receptor, Protein Kinase B/Akt, and Glioma Response to Erlotinib," Journal of the National Cancer Institute, vol. 97, No. 12, Jun. 15, 2005, pp. 880-887, XP002481862.
Hu, X et al., "mTOR Promotes Survival and Astrocytic Characteristics induced by Pten/Akt Signaling in Glioblastoma," Neoplasia, vol. 7, No. 4, Apr. 2005, pp. 356-368, XP002526505.
International Search Report and Written Opinion mailed Jul. 17, 2009 in International Application No. PCT/US2009/033691 (15 pages).
Mellinghoff, I. K. et al., "Molecular Determinants of the Response of Glioblastomas to EGFR Kinase Inhibitors," New England Journal of Medicine, vol. 353, No. 19, Nov. 10, 2005, pp. 2012-2024, XP003005372.
Sun, Mei et al., "AKT1/PKBα Kinase is Frequently Elevated in Human Cancers and its Constitutive Activation is Required for Oncogenic Transformation in NIH3T3 Cells," American Journal of Pathology, vol. 159, No. 2, Aug. 2011 pp. 431-437, XP002526503.
Wendel, H.G. et al., "Survival Signalling by Akt and eIF4E in Oncogenesis and Cancer Therapy," Nature, vol. 428, Mar. 18, 2004, pp. 332-337, XP002996035.

* cited by examiner

*Primary Examiner* — Sean Aeder
(74) *Attorney, Agent, or Firm* — Gilberto M. Villacorta; Jeffrey R. Lomprey; Foley & Lardner LLP

(57) ABSTRACT

Interestingly, for prognosis, the significant biomarkers for Gefitinib-treated GBM patients (RTOG 0211) appeared to differ compared to historical, RT and non-Gefitinib-treated GBM patients. In Gefitinib-treated patients, those with higher levels of nuclear pAKT driven by PTEN loss, higher levels of nuclear pMAPK, and lower levels of nuclear pmTOR had significantly worse clinical outcomes. In contrast, in non-Gefitinib-treated patients, patients with PTEN-deficiency, and higher levels of EGFRvIII, total EGFR, IGFR1, NFkB and lower levels of nuclear Survivin appeared to have adverse clinical outcomes, highlighting the treatment-dependency of these biomarkers.

4 Claims, 19 Drawing Sheets

Figure 1.

| Biomarker | Antibody (species) | Vendor | Catalog # | Localization | titer | Optimal [c] |
|---|---|---|---|---|---|---|
| pAKT | Mouse | CST | 4051 | Nuclear | 1:25 | 2 µg/ml |
| PTEN | Rabbit | CST | 9559 | Cyto and Nuclear | 1:25 | 0.8 µg/ml |
| EGFR VIII | Rabbit | Affinity BioReagents | PA1-37610 | Cytoplasmic | 1:50 | 1.6 µg/ml |
| EGFR | Mouse | DAKO | M3563 | Cytoplasmic | 1:100 | 5.9 µg/ml |
| IGF-1R | Rabbit | CST | 3027 | Cytoplasmic | 1:50 | 4 µg/ml |
| pMAPK | Rabbit | CST | 4376 | Cyto and Nuclear | 1:50 | 3 µg/ml |
| pmTOR | Rabbit | Abcam | ab51044 | Nuclear | 1:100 | 100 µg/ml |
| Survivin | Rabbit | CST | 2808 | Nuclear | 1:100 | 1.61 µg/ml |
| NFkB | Rabbit | Lab Vision | RB-9034-P | Cytoplasmic | 1:500 | 8 µg/ml |
| phospho-p65 | rabbit polyclonal | CST | 3037 | Nuclear | 1:50 | -- |
| MGMT | mouse monoclonal | Santa Cruz | sc-56432 | Nuclear | 1:50 | -- |
| Src | Rabbit | CST | 2108 | Cytoplasmic | 1:100 | 4.34 µg/ml |

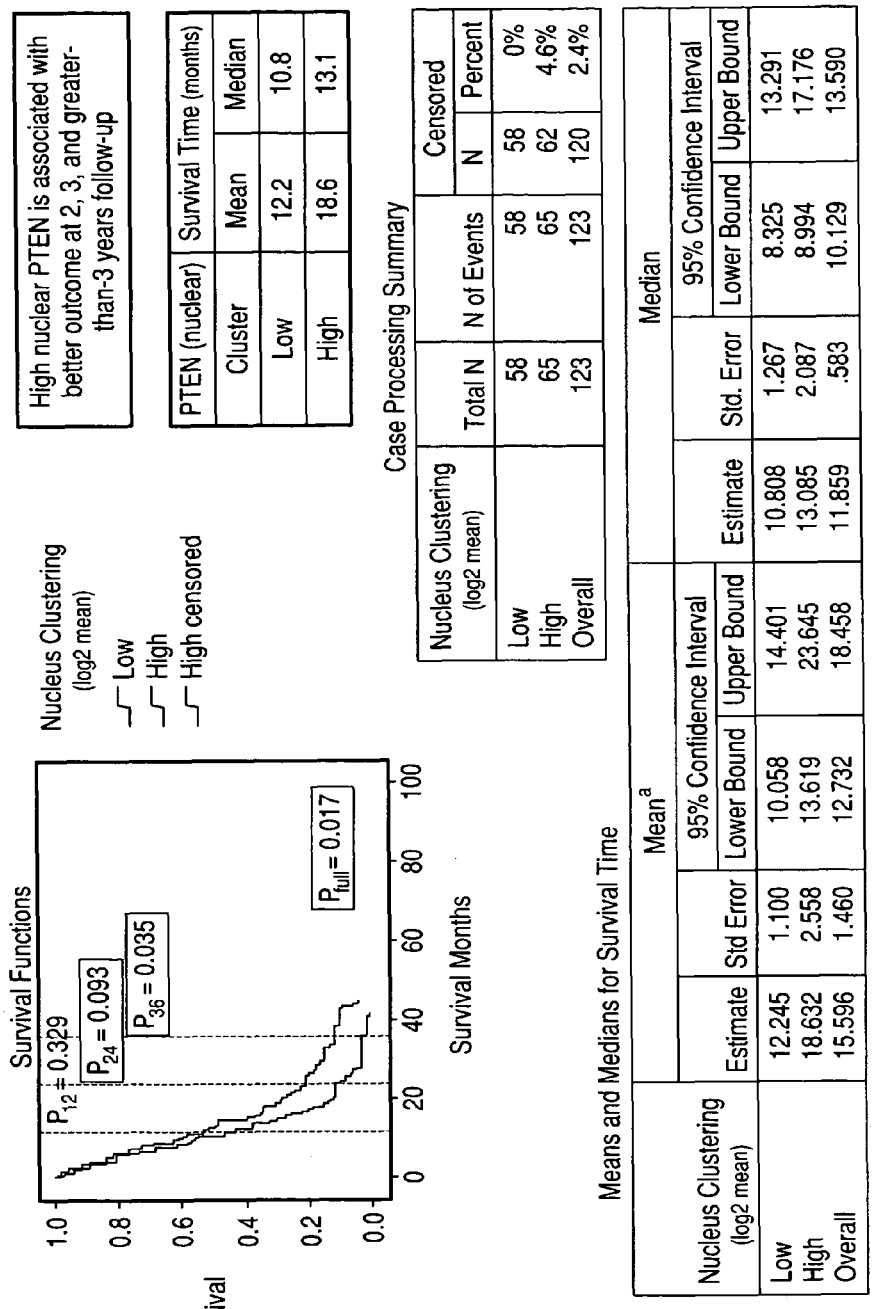

Figure 3

Summary of Survival Analysis: PTEN

| Biomarker | Localization | Clusters (N) | Parameter | Survival (follow-up time in years) | K-M Analysis p-value | Trends |
|---|---|---|---|---|---|---|
| PTEN | Nuclear | Low (58) High (65) | Survival time | 1 | 0.329 | Higher levels = Better outcome |
| | | | | 2 | 0.093 | |
| | | | | 3 | 0.035 | |
| | | | | > 3 | 0.017 | |
| | | | Progression-free time | 1 | 0.974 | No significant trend observed |
| | | | | 2 | 0.449 | |
| | | | | 3 | 0.219 | |
| | | | | > 3 | 0.219 | |
| | Non-nuclear | Low (28) Intermediate (64) High (31) | Survival time | 1 | 0.374 | No significant trend observed |
| | | | | 2 | 0.433 | |
| | | | | 3 | 0.365 | |
| | | | | > 3 | 0.241 | |
| | | | Progression-free time | 1 | 0.927 | No significant trend observed |
| | | | | 2 | 0.860 | |
| | | | | 3 | 0.981 | |
| | | | | > 3 | 0.981 | |

EGFRvIII (non-nuclear) on Array 8 (log2-transformed): Progression-Free Time (means)

Summary of Survival Analysis: EGFRvIII

| Biomarker | Localization | Clusters (N) | Parameter | Survival (follow-up time in years) | K-M Analysis p-value | Trends |
|---|---|---|---|---|---|---|
| EGFRvIII | Non-nuclear | Low (19) Intermediate (75) High (42) | Survival time | 1 | 0.766 | No significant trend observed |
| | | | | 2 | 0.152 | |
| | | | | 3 | 0.226 | |
| | | | | > 3 | 0.265 | |
| | | | Progression-free time | 1 | 0.095 | Lower levels = Better outcome |
| | | | | 2 | 0.040 | |
| | | | | 3 | 0.046 | |
| | | | | > 3 | 0.050 | |

Summary of Survival Analysis: EGFR

| Biomarker | Localization | Clusters (N) | Parameter | Survival (follow-up time in years) | K-M Analysis p-value | Trends |
|---|---|---|---|---|---|---|
| EGFR | Non-nuclear | Low (77) Intermediate (34) High (11) | Survival time | 1 | 0.080 | No significant trend observed |
| | | | | 2 | 0.623 | |
| | | | | 3 | 0.400 | |
| | | | | > 3 | 0.400 | |
| | | | Progression-free time | 1 | 0.078 | Lower levels = Better outcome |
| | | | | 2 | 0.015 | |
| | | | | 3 | 0.015 | |
| | | | | > 3 | 0.015 | |

Figure 18. Src – Overall survival
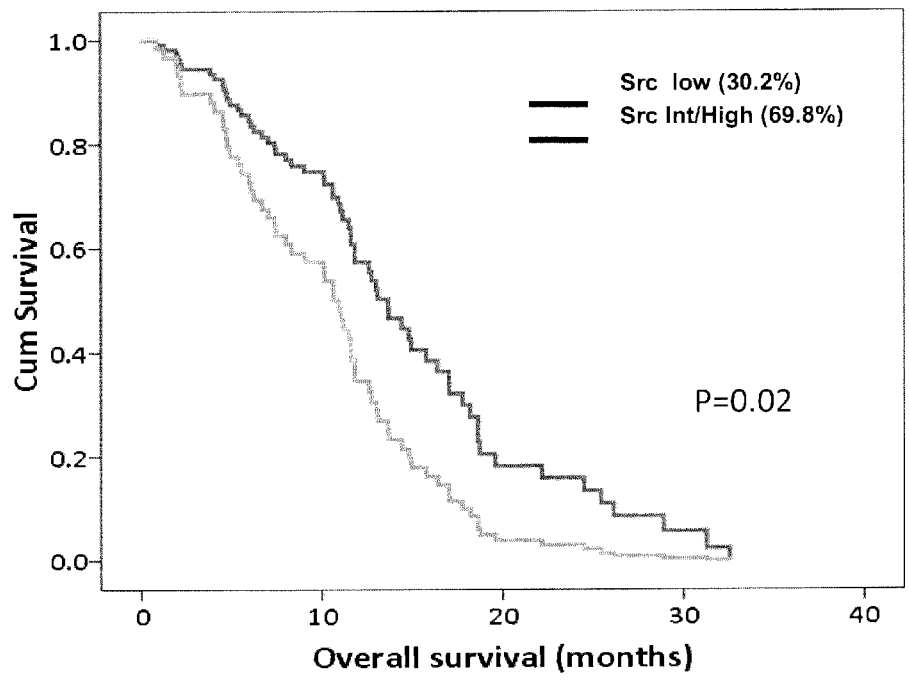

Figure 19. Multivariate Analysis: Overall Survival

|        | coef | exp(coef) | se(coef) | z    | p    |
|--------|------|-----------|----------|------|------|
| egfr2  | 0.72 | 2.05      | 0.39     | 1.82 | 0.07 |
| NFKB2  | 0.63 | 1.87      | 0.39     | 1.60 | 0.11 |
| src    | 0.63 | 1.88      | 0.34     | 1.85 | 0.06 |
| age10  | 0.35 | 1.41      | 0.16     | 2.22 | 0.03 |

|          | coef | exp(coef) | se(coef) | z    | p    |
|----------|------|-----------|----------|------|------|
| risk2int | 0.72 | 2.06      | 0.38     | 1.91 | 0.06 |
| risk3hi  | 1.22 | 3.40      | 0.49     | 2.51 | 0.01 |
| age10    | 0.40 | 1.50      | 0.13     | 3.03 | 0.00 |

Low has 10, Int has 41, and High has 10 observations.

CORRELATION OF MOLECULAR MARKERS WITH CLINICAL OUTCOME IN GBM PATIENTS RADIATION TREATED WITH OR WITHOUT GEFITINIB

CROSS-REFERENCE TO RELATED APPLICATIONS

The present application claims the priority benefit under 35 U.S.C. §119(e) to U.S. Provisional Application No. 61/136,642, filed Sep. 22, 2008, which is hereby incorporated by reference in its entirety.

GOVERNMENT FUNDING

At least a portion of this work was supported by grant number (RTOG U10 CA21661, CCOP U10 CA37422, Stat U10 CA32115) from the National Cancer Institute; the RTOG seed grant program, Brain Tumor Funders Collaborative Grant, and NIH/NCI-RO1CA108633. The federal government may have certain rights to this invention.

BACKGROUND OF THE INVENTION

Glioblastoma Multiforme (GBM) is the most common malignant brain tumor of adults and is among the most lethal of all cancers. Analysis of large clinical databases demonstrates clinical prognostic groups of glioblastoma patients, suggesting considerable biological heterogeneity(Curran W J, 1993 J Natl Cancer Ins 85:704-710;Scott C B, 1998 Int J Radiat Oncol Biol Phys. 1998 Jan. 1;40(1):51-5. Recent data suggest that morphologically indistinguishable glioblastomas have distinct classes of causal oncogene activation and downstream signaling pathway deregulation that may affect survival and response to therapy (Mischel P S, 2003 Cancer Biol Ther 2(3)242-7; Mischel P S, 2003 Brain Pathol 13(1) 52-61; Mischel P S, 2003 Oncogene 22(15)2361-73; Mischel, 2003 #3120; Shai, 2003 #3161; Chakravarti, 2001 Clin Cancer Res (1)2387-2395. Deregulation of the PI3K/Akt pathway signaling, which promotes malignant transformation, tumor progression and radiation-resistance in pre-clinical models, is common in glioblastomas (Choe, 2003 Cancer Res 63:2742-2746; Chakravarti, 2003 #3229; Chakravarti, 2004 Oncogene 23(45)7494-506; J Clin Oncol 22(10)1926-33; Int J Radiat Oncol Biol Phys 58(3)927-31).

It is an object of the present invention, therefore, to identify biomarkers that have prognostic value for GBM and to develop assays useful for identifying patients that may be suitable for targeted therapies.

SUMMARY OF THE INVENTION

The present invention is directed to a method of determining a prognosis of a patient comprising assessing the concentration of one or more protein biomarkers selected from the group consisting of PTEN, EGFRvIII, EGFR, IGF-1R, and NFkB in a tissue specimen obtained from the patient in which high levels of PTEN, EGFRvIII, EGFR, IGF-1R, and/or NFkB indicate a relatively poor prognosis for the patient when treated with radiation therapy alone. In a particular embodiment of the invention the patient suffers from brain cancer, and the brain cancer may be glioblastoma.

The invention is further directed to a method of determining a prognosis of a patient comprising: assessing the relative concentrations of two or more protein biomarkers selected from the group consisting of PTEN, EGFRvIII, EGFR, IGF-1R, and NFkB in a tissue specimen obtained from the patient in which high levels of PTEN, EGFRvIII, EGFR, IGF-1R and/or NFkB indicate a relatively poor prognosis for the patient when treated with radiation therapy alone.

The invention is also directed to a method of determining a prognosis of a patient comprising: assessing the concentration (or relative concentration) of one or more protein biomarkers selected from the group consisting of pAKT, pmTOR, and pMAPK in a tissue specimen obtained from the patient in which high levels of nuclear pAKT, nuclear pMAPK, and/or low levels of nuclear pmTOR indicate a relatively poor prognosis for the patient when treated with radiation therapy in combination with gefitinib.

In a particular embodiment of the invention a method is described for determining a prognosis of a patient by assessing the relative concentration of one or more biomarkers in a tissue sample comprising: (a) incubating the tissue sample with a first stain that specifically labels a first marker defined subcellular compartment, a second stain that specifically labels a second marker defined subcellular compartment, and a third stain that specifically labels a biomarker; (b) obtaining a high resolution image of each of the first, the second and the third stain in the tissue sample; (c) assigning a pixel of the image to a first compartment based on the first stain intensity, a second compartment based on the second stain intensity, or to neither a first nor second compartment; (d) measuring the intensity of the third stain in each of the pixels assigned to either the first or the second compartment or both; (e) determining a staining score indicative of the concentration of the biomarker in the first or the second compartment or both; and (f) plotting the biomarker concentration in relationship to a second biomarker concentration thereby providing a determination of the patient's prognosis. Typically, the tissue sample is obtained from a patient suffering from brain cancer, most likely, glioblastoma multiforme. Also the one or more biomarkers may be selected from the group consisting of pAKT, PTEN, EGFRvIII, EGFR, IGF-1R, pmTOR, pMAPK, survivin, or NFkB. One of the subcellular compartments may be cytoplasm, for which GFAP can be used as a stain that specifically labels this subcellular compartment.

The invention also provides a kit comprising: (a) a first stain specific for pAKT, PTEN, EGFRvIII, EGFR, IGF-1R, pmTOR, pMAPK, survivin, and/or NFkB; (b) a second stain specific for a first subcellular compartment of a cell; and (c) instructions for using the kit. The second stain is preferably GFAP.

Another aspect of the invention relates to a method of identifying a patient suitable for treatment with gefitinib in combination with radiation therapy, comprising: assessing the relative concentration of one or more biomarkers in a tissue specimen obtained from the patient wherein high levels of one or more biomarkers indicates the patient is likely to benefit from treatment. The term "relative concentration" means that the protein biomarker expression levels of a particular patient are compared with a plurality of patients. The overall results can be separated in most cases to relatively "high" expression levels, relatively "low" expression levels, and "intermediate" levels. Individual patients can then be assigned to one group or one of the other groups. Preferably, the one or more biomarkers, whose expression levels are assessed, are chosen from the group consisting of pAKT, PTEN, EGFRvIII, EGFR, IGF-1R, pmTOR, pMAPK, survivin, and/or NFkB.

It is also an objective of the invention to provide a method of determining a prognosis of a patient comprising: assessing the concentration (or the relative concentration) of one or more protein biomarkers selected from the group consisting of pAKT, PTEN, EGFRvIII, EGFR, IGF-1R, pmTOR, pMAPK, survivin, and/or NFkB in a tissue specimen obtained from the patient in which an intermediate level of expression of IGF-1R or NFkB or a high cytoplasmic to nuclear ratio of pAKT indicate a relatively poor prognosis for the patient when treated with radiation therapy alone.

It is a further objective of the invention to provide a method of determining a prognosis of a patient comprising: assessing the concentration (or the relative concentration) of one or more protein biomarkers selected from the group consisting of pAKT, PTEN, EGFRvIII, EGFR, IGF-1R, pmTOR, pMAPK, survivin, and/or NFkB in a tissue specimen obtained from the patient in which a high nuclear pMAPK or intermediate cytopslasm to nuclear PTEN ratio indicate a relatively good prognosis for the patient when treated with radiation therapy alone.

Yet another objective of the invention is to provide a method of determining a prognosis of a patient comprising: assessing the concentration (or the relative concentration) of one or more protein biomarkers selected from the group consisting of Src, pAKT, PTEN, EGFRvIII, EGFR, IGF-1R, pmTOR, pMAPK, survivin, and/or NFkB in a tissue specimen obtained from the patient in which an intermediate level of EGFR, high level of NFkB and/or intermediate to high Src level indicate a relatively poor prognosis for the patient when treated with radiation therapy combined with gefitinib.

Yet another objective of the invention is to provide a method of determining a prognosis of a patient comprising: assessing the concentration (or the relative concentration) of one or more protein biomarkers selected from the group consisting of Src, pAKT, PTEN, EGFRvIII, EGFR, IGF-1R, pmTOR, pMAPK, survivin, and/or NFkB in a tissue specimen obtained from the patient in which relatively high or low EGFR levels, low Src levels and/or low to intermediate NFkB indicate a relatively good prognosis for the patient when treated with radiation therapy combined with gefitinib.

Still another objective of the invention is to provide a method of determining a prognosis of a patient comprising: assessing the concentration (or the relative concentration) of one or more protein biomarkers selected from the group consisting of Src, pAKT, PTEN, EGFRvIII, EGFR, IGF-1R, pmTOR, pMAPK, survivin, and/or NFkB in a tissue specimen obtained from the patient in which expression or AQUA® score of each biomarker on a continuous scale is put into a Cox regression model for continuous variables resulting in a calculation of overall patient risk.

Another objective of the invention is to provide a method of determining a prognosis of a patient comprising: assessing the concentration (or the relative concentration) of one or more protein biomarkers selected from the group consisting of Src, pAKT, PTEN, EGFRvIII, EGFR, IGF-1R, pmTOR, pMAPK, survivin, and/or NFkB in a tissue specimen obtained from the patient in which expression or AQUA® score of each biomarker is first categorized based on optimal univariate cutpoints, then applied to a Cox regression model for categorical variables resulting in a calculation of overall patient risk.

Still another objective of the invention is to provide a method of determining prognosis or relative survival risk of a patient treated with radiation therapy combined with gefitinib comprising assessing the concentration, or the relative concentration of EGFR, NFkB and SRC in a tissue specimen obtained from the patient, wherein positive expression of all biomarkers is indicative of a high survival risk; no expression of all biomarkers is indicative of low survival risk; and positive expression of any two biomarkers is indicative of moderate survival risk

BRIEF DESCRIPTION OF THE FIGURES

FIG. 1 is a summary of detection reagents used for determining biomarker AQUA® scores.

FIG. 2 is a Kaplan-Meier analysis of survival based on PTEN scores from Array 8.

FIG. 3 is a summary table of survival analysis based on PTEN analysis of Array 8.

FIG. 5 is a summary table of survival analysis based on EGFRvIII analysis of Array 8.

FIG. 7 is a summary table of survival analysis based on EGFR analysis of Array 8.

FIG. 18 is a Kaplan-Meier analysis of survival based on Src scores from Array 19.

FIG. 19 is a multivariate risk model for overall survival based on biomarker scores from Array 19.

PREFERRED EMBODIMENTS OF THE INVENTION

Figure 4:
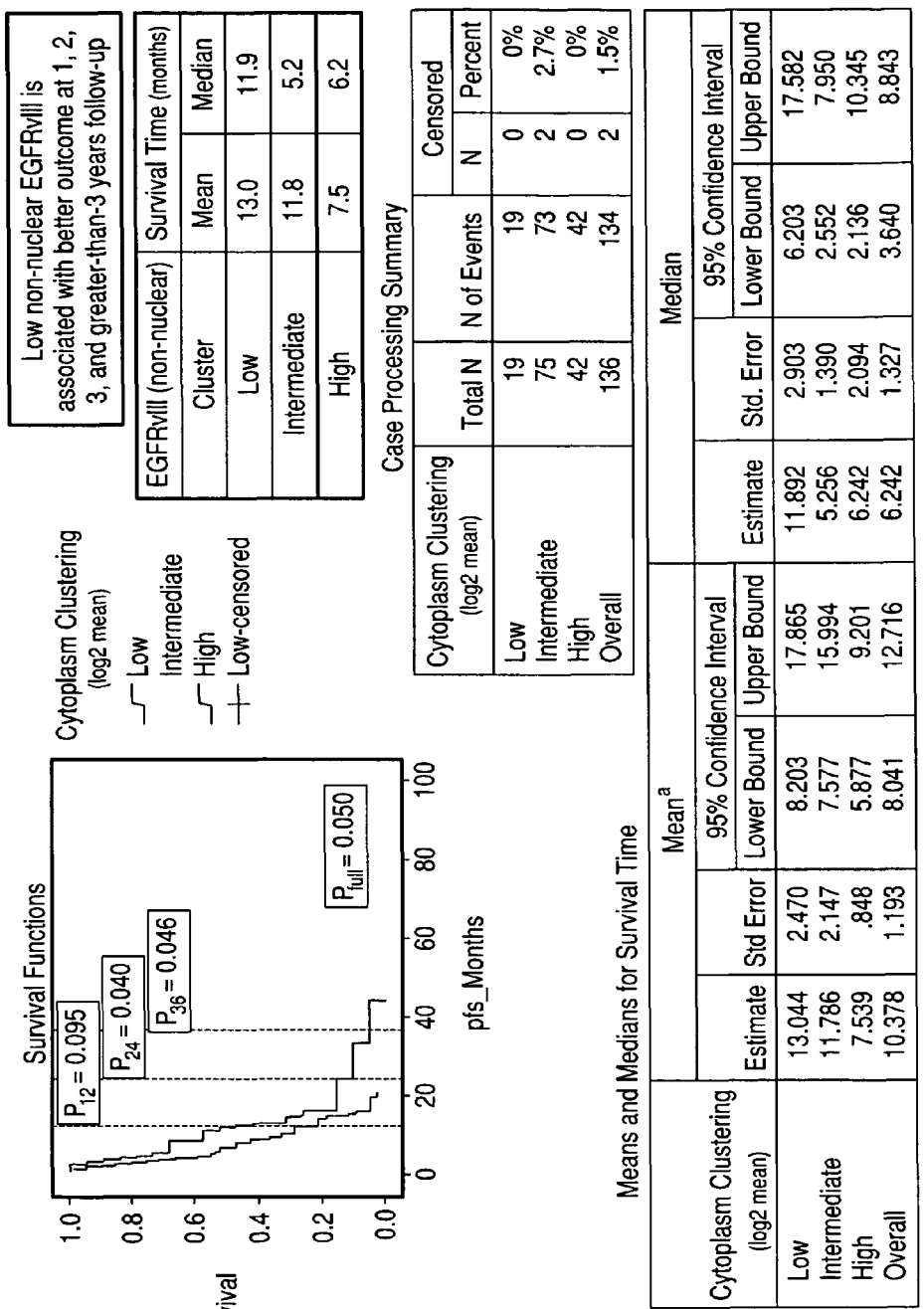
FIG. 4 is a Kaplan-Meier analysis of survival based on EGFRvIII scores from Array 8.
Figure 6:
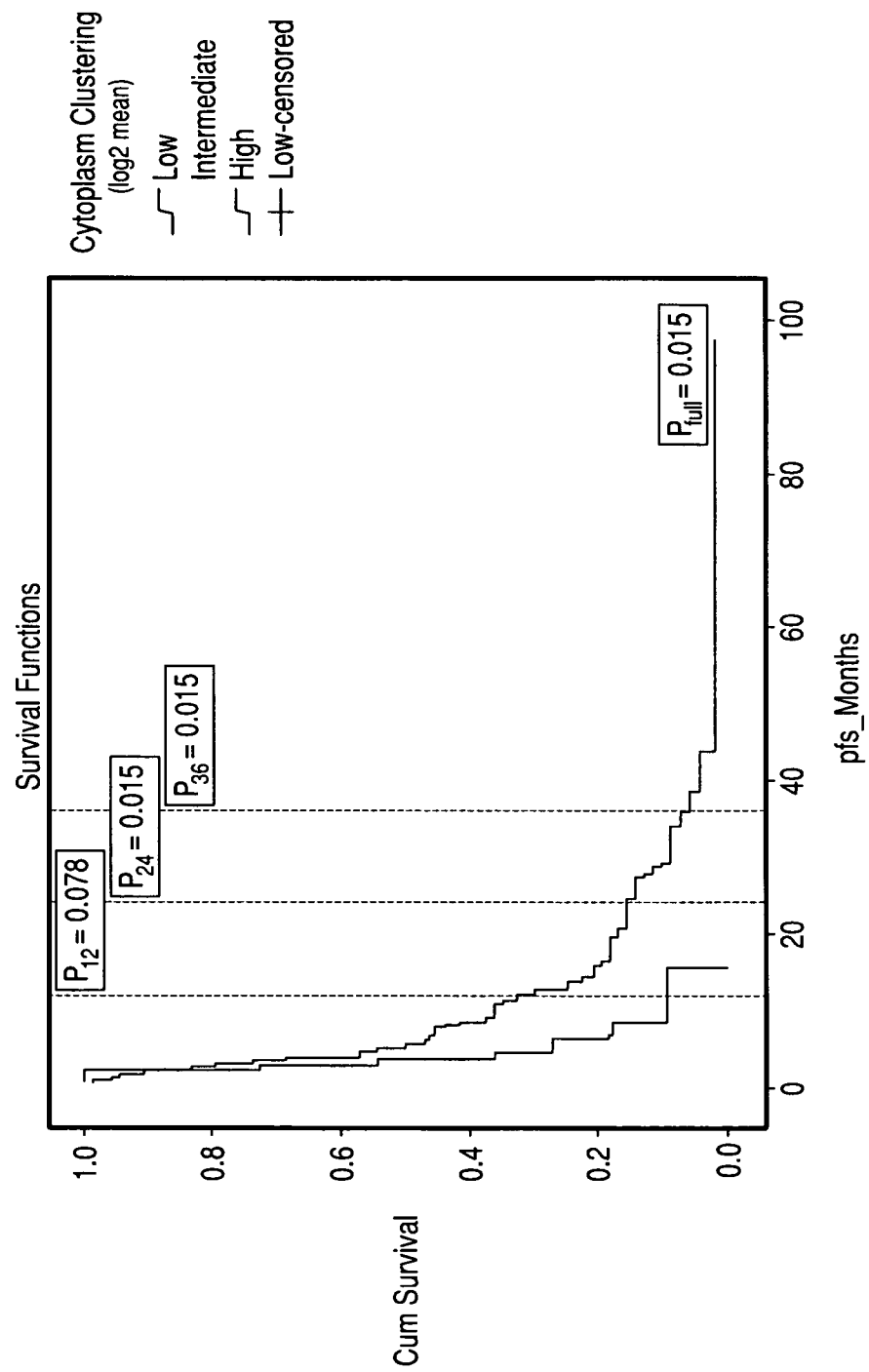
FIG. 6 is a Kaplan-Meier analysis of survival based on total EGFR scores from Array 8.

Glioblastoma is the most common malignant brain tumor of adults, and is among the most lethal of all cancers (Gurney, 2001; Mischel, 2003; Walker, 1978; Walker, 1980; all supra). Despite aggressive surgical approaches, optimized radiation therapy regimens and a wide variety of cytotoxic chemotherapies, the median survival of glioblastoma patients is one year from the time of diagnosis. Clearly, new approaches to the understanding and treatment of glioblastoma are needed.

The past decade has clearly demonstrated that all glioblastomas are not the same; there are distinct clinical presentations that are associated with different sets of molecular alterations (Mischel, 2003; Nutt, 2003 Cancer Research 63(7) 1602-7; von Deimling, 1993 Brain Pathol 3(1)19-26; Chakravarti, 2002 Cancer Research 62:200-207. For example, glioblastoma that arise de novo (primary glioblastomas) and those that arise from lower grade gliomas (secondary glioblastomas) often look identical microscopically, but contain distinctive sets of molecular alterations (Frederick, 2000; Kleihues, 2002 J Neuropathol Exp Neurol 61(3) 215-25; Kleihues, 1999 Neuro Oncol 1(1)44-51; Rao, 2003). Recent work, including work from the present inventors, clearly indicates that there are additional molecular subtypes of glioblastomas that contain distinctive patterns of oncogene/tumor suppressor gene changes and resultant pathway alterations that can potentially be targeted. Recognition of the signaling pathway alterations associated with these molecular subsets is likely to be the key feature in promoting the application of targeted inhibitor therapy to glioblastoma patients.

The biological behavior of many cancers appears to be driven by deregulated signaling pathways (Mischel, 2003; Neshat, 2001 Proc Natl Acad Sci 98(18)10314-9; Chakravarti, 2002; Chakravarti, 2002; Sawyers, 2002 Cancer Cell 1(1)13-15; Sawyers, 2002 Curr Opin Investig Drugs 3(3)478-81). Paradoxically, these deregulated pathways may also be their "Achilles Heel." Non-cancerous cells have "back-up" mechanisms that allow them to survive and even proliferate in the face of disruption of a single pathway. In contrast, cancer cells may become dependent upon on these constitutively activated pathways (Mischel, 2003; Neshat, 2001; Chakravarti, 2002; Sawyers, 2002).

Kinase inhibitors have demonstrated dramatic success for the treatment of patients with some types of cancer. STI-571, an inhibitor of the Abl and c-Kit kinases has proven to be a highly effective, non-toxic therapy for patients with chronic myelogenous leukemia (which commonly bear constitutively active BCR-ABL fusion tyrosine kinases) and gastrointestinal stromal tumors (which often contain gain of function mutations of the c-KIT tyrosine kinase) (Sawyers, 2002; Druker, Oncogene 21(56)8541-6, 2002; Druker, 2001; Joensuu, 2002 Med Klin 97 Suppl 1:28-30). Patients may ultimately develop resistance to these drugs as single agents; however, these studies provide proof of principle that small molecule inhibitors can potentially provide substantial clinical benefit for cancer patients. Glioblastomas contain patterns of oncogene activation and tumor suppressor gene loss that drive their biological and clinical behavior. The resultant deregulated signaling pathways may form the basis for distinct classes of glioblastomas that are targetable with pathway specific inhibitors.

For example, PI3K is a lipid kinase that promotes diverse biological functions including cellular proliferation, survival and motility (Vivanco, 2002 Nat Rev Cancer 2(7)489-501. The PI3K signaling pathways is frequently deregulated in glioblastoma (Choe, 2003 Ermoian, 2002 Clin Cancer Res 8(5)1100-6, often in combination with the ERK pathway, and mouse genetic studies suggest a causal role of this pattern (Holland, 2000 #588). The PI3K pathway (and RAS/ERK pathway) can become deregulated on the basis of oncogene activation and tumor suppressor gene losses that are commonly seen in glioblastoma. Up to 40% of glioblastomas contain alterations of the PTEN tumor suppressor gene, a negative regulator of PI3K signaling, which results in constitutive activation of the PI3K pathway (Ermoian, 2002 #2826). Upstream of PI3K, the epidermal growth factor receptor (EGFR) is commonly over-expressed, frequently in association with its constitutively activated EGFRvIII variant (and other variants), which may lead to deregulated PI3K and RAS/ERK signaling Other receptor tyrosine kinases such as PDGFR and c-MET are also commonly over-expressed in glioblastomas, and may deregulate these same pathways (Frederick, 2000; Kleihues, 2002; Kleihues, 1999; Mischel, 2003; Rao, 2003; von Deimling, 1993; Watanabe, 1996; Abounader, 2002; Abounader, 2001). The PI3K and RAS/ERK pathways connect richly to other signaling cascades, thereby integrating signals associated with other cell surface events, stress activation pathways and extracellular matrix proteins. RAC1 is one such protein that links PI3K and RAS signaling with integrin-linked signaling, potentially playing a key role in promoting glioblastoma growth and survival (Senger, 2002). Therefore, the PI3K and ERK signaling pathways, and associated molecules, provide important therapeutic targets.

Pathways can be targeted with small molecule inhibitors, as well as with monoclonal antibodies directed against cell surface receptors (either armed or unarmed) (Lorimer, 2001; Wikstrand, 1998; Wikstrand, 1997; Wikstrand, 1995; Wikstrand, 1999) and oncolytic viruses (Wilcox, 2001 #3204). In particular, the EGFR inhibitors ZD1839 and OSI-774, the mTOR inhibitors rapamycin and its analogue CCI-779 and the farnesyl transferase inhibitor R115777 have demonstrated promising results in some glioblastoma patients in clinical trials (up to 20%). The critical question, one addressed by the present invention, is determining the molecular profile of patients that benefit from kinase inhibitors.

Analysis of the PI3K and ERK pathways in glioblastoma biopsies was done using an immunohistochemical analysis of a tissue microarray of primary glioblastomas with hierarchical clustering and multidimensional scaling, as well as univariate and multivariate analyses to dissect the PI3K and ERK pathways in vivo. It was demonstrated that PTEN loss, which antagonizes PI3K pathway activation, was highly correlated with activation of the main PI3K effector Akt in vivo. It was also shown that Akt activation is significantly correlated with phosphorylation of mTOR, FKHR and S6, which are thought to promote its effects. Expression of the mutant epidermal growth factor receptor EGFRvIII is also tightly correlated with phosphorylation of these effectors, demonstrating an additional route to PI3K pathway activation in glioblastomas in vivo. In contrast wild type EGFR overexpression correlated with ERK activation. These results from the univariate and multivariate analyses are consistent with the presumed relationships between PTEN and other known components of the PI3K and ERK signaling pathways (Choe, 2003).

These pathway proteins can therefore be used as biomarkers for determining the prognosis or survival risk of cancer patients, as well as determining which patients are suitable for pathway-specific therapeutics. Detecting expression levels of biomarkers in a tumor sample (i.e., a sample containing cancer cells) may be accomplished by detecting altered RNA or protein levels of a particular component when compared to a control level. Relevant controls include RNA or protein levels in a non-cancer cell of the same type as a cancer cell, or RNA or protein levels in a cancer cell prior to receiving an indicated treatment. Such control levels may be measured concomitantly with detecting levels of biomarkers in a cancer cell or test cell, before or after detecting levels of biomarker components in a cancer cell or test cell, or may constitute known levels in a control cell such that repeated determination is not required.

Expression of biomarkers may be determined by detecting protein or RNA using techniques well known to one skilled in the art. The invention may be successfully performed using any suitable detection technique that generates a quantifiable result.

For example, protein expression levels may be determined by immunoassays, Western Blot analysis, or two-dimensional gel electrophoresis. Representative immunoassays include immunohistochemistry (including tissue microarray formats), fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). Protein levels may also be detected based upon detection of protein/protein interactions, including protein/ antibody interactions using techniques such as Fluorescence Correlation Spectroscopy, Surface-Enhanced Laser Desorption/Ionization Time-Of-flight Spectroscopy, and BIA-CORE® technology.

RNA expression levels may be determined using techniques such as reverse-transcriptase polymerase chain reaction (RT-PCR), quantitative reverse-transcriptase polymerase chain reaction (QRT-PCR), TAQMAN® real-time-PCR fluorogenic assay, serial analysis of gene expression (SAGE) (see e.g., Velculescu et al., Cell, 1997, 88, 243-251; Zhang et al., Science, 1997, 276, 1268-1272, and Velculescu et al., Nat. Genet., 1999, 23, 387-388), microarray hybridization, Northern Blot analysis, and in situ hybridization.

According to the present invention, levels of expressed protein or RNA of a biomarker in a tumor sample are quantified for comparison with control levels. For in situ analysis, the AQUA® pathology system may be used. In brief, monochromatic, high-resolution (1,024×1,024 pixel; 0.5 μm) images are obtained of each histological sample. Cellular or subcellular (e.g., nuclei, cytoplasm, etc.) areas of interest are identified by creating a mask (e.g., a tumor mask), and the signal within the mask is then used to identify the cellular or subcellular area of interest. AQUA® scores are measured as the intensity of expressed protein within the area of interest and are typically normalized to the mask. AQUA® scores for duplicate tissue cores can be averaged to obtain a mean AQUA® score for each sample.

Biomarkers may also be detected by assessing localization of biomarkers in the tissue and within cancer cells. Techniques that may be used for detecting localization of biomarkers are known in the art, and include numerous immunoassays for detecting levels of protein expression or levels of activated proteins, as described herein above. In some aspects of the invention, subcellular localization of a biomarker ise assessed in combination, either sequentially or contemporaneously, with levels of additional biomarkers. As for measuring levels of expression of biomarkers, levels of protein localized to a particular subcellular compartment are quantified for comparison to control levels. Thus, in one aspect of the invention provides a method of determining a prognosis of a patient by assessing the relative levels of one or more biomarkers in subcellular compartments or specializations of a tissue sample by (a) incubating the tissue sample with a stain that specifically labels a first marker that defines a first subcellular compartment or specialization, a second stain that specifically labels a second marker that defines a second subcellular compartment or specialization, and a third stain that specifically labels a biomarker; (b) obtaining a high resolution image of each of the first, second, and third stains in the tissue sample; (c) assigning each pixel of the image to the first or second subcellular compartments or specializations based upon the first and second stain intensities, respectively; (d) measuring the intensity of the third stain in each of the pixels of the image; (e) determining a staining score indicative of the concentration of the biomarker in the first and second subcellular compartments or specializations; and (f) predicting prognosis of the cancer patient based upon the level of the biomarker in the first or second subcellular compartment or specializations.

For example, using the AQUA® pathology system, nuclear protein may be quantified as follows. The tissue may be "masked" using cytokeratin in one channel to identify the area of tumor and to remove the stromal and other non-tumor material from analysis. Then an image is taken using DAPI to define a nuclear compartment. The pixels within the mask and within the DAPI-defined compartment are defined as tumor nuclei pixels. The intensity of expression of the protein is measured using a third channel. The intensity of protein expression in the defined subset of pixels divided by the number of pixels (to normalize the area from sample to sample) gives an AQUA® score. This score is directly proportional to the number of molecules of the protein per unit area of tumor nuclei. This technique, is described in detail Camp et al., Nat Med., 2002, 8:1323-1327. See also U.S. Pat. No. 7,219,016. The disclosures of the foregoing references are incorporated herein be reference in their entireties, particularly with respect to the disclosure of techniques for determining AQUA® scores in cellular samples, which may also be used in the methods of the present invention.

Localization of biomarkers within cells may also be determined using subcellular fractionation techniques, as known in the art, when used in conjunction with immunoassay techniques. For some biomarkers, detecting changes in levels of expression yields a similar result whether such levels are measured in whole cells or in a subcellular compartment (e.g., nuclear or cytoplasmic expression). For these biomarkers, detection may be alternatively be performed by assessing expression in tumor cells, tumor cell nuclei, tumor cell cytoplasm, or other subcellular compartment of tumor cells, as convenient.

When assessing a level of any one of the above-noted criteria (e.g., a level of RNA or protein of a biomarker or other tumor marker, a level of protein expression, a level of subcellular localization of a biomarker), the "relative concentration" or "relative level" is assessed by comparing the concentration or level of the biomarker to the concentration or level of the same biomarker in a control sample or a reference standard. For example, a relevant control may comprise a sample taken from a tumor-bearing patient and from a same tissue and analogous region on the contralateral side of the patient. As another control, a sample may be taken from a same tissue and analogous region from a similarly situated (age, gender, overall health, etc.) patient who lacks a tumor. In the case of assessment of treatment-dependent response, post-treatment effects may also be ascertained through parallel analysis of a pre-treatment control sample.

When quantifying a level of any of the above-described criteria for defining increased or decreased biomarker expression, a difference when assessed relative to a control level is identified as a difference of at least about two-fold greater or less than a control level, or at least about five-fold greater or less than a control level, or at least about ten-fold greater or less than a control level, at least about twenty-fold greater or less than a control level, at least about fifty-fold greater or less than a control level, or at least about one hundred-fold greater or less than a control level. A difference in the above-noted criteria when assessed relative to a control level may also be observed as a difference of at least 5%, 10%, 20% compared to a control level, such as at least 30%, or at least 40%, or at least 50%, or at least 60%, or at least 70%, or at least 80%, or at least 90%, or at least 100%, or more.

The references cited herein are each incorporated by reference in its entirety.

Study Group

The Radiation Therapy Oncology Group (RTOG) Study #0211 Phase I/II Study of Gefitinib+Radiation for Newly Diagnosed Glioblastoma (GBM) revealed that the addition of Gefitinib to radiation was well-tolerated, but survival was not significantly improved compared to historical controls (AS-TRO 2006). Based on data from a retrospective analysis of recurrent GBM treated with EGFR TKIs, subgroups with specific molecular signatures were analyze to determine which are more likely to benefit from anti-EGFR therapies. The present application is the first report to evaluate molecular correlates of clinical outcome in newly diagnosed GBM treated by anti-EGFR therapies and represents the most comprehensive correlative analysis performed on GBM patients treated by anti-EGFR therapies.

Detection of activation of pathways along the PI3K and ERK axis will likely enable the prediction of patient outcome (prognosis) as well as resistance to/benefit from conventional therapies and molecularly based targeted therapies (prediction), in particularly radiation with or without Gefitinib treatment.

Methods

Tissue blocks were prospectively collected from RTOG 0211 cases (Array 19) as well as historical, RT treated cases (Array 8), which were used to generate tissue microarrays (TMAs). The predictive values of molecules integral to EGFR signaling were examined. Phosphorylation and/or expression patterns of EGFR, EGFRvIII, PTEN, p-Akt, p-mTOR, p-S6, p-Erk, Survivin, pSrc, IGFR1, NFkB were evaluated using AQUA® analysis.

Results

The resulting data, based on analysis of 120+ GBM patients treated on previous RTOG studies prior to the temozolomide era indicate that activation of this pathway at distinct points appears to be significantly associated with patient outcome. Further, in the setting of molecularly-based targeted therapies, such as EGFR tyrosine kinase inhibitors (TKIs), our preliminary data, based on 90+ newly-diagnosed GBM patients treated on the clinical study RTOG 0211 with the EGFR TKI, Gefitinib, in combination with radiation, seems to suggest distinct predictive biomarkers of outcome compared to patients treated by radiation alone in historical RTOG clinical studies. Findings suggest that activation of critical signaling pathways along the PI3K and ERK axis can mediate resistance to both conventional (radiation, temozolomide) and molecularly-based targeted therapies. Our preliminary preclinical data appear to not only support activation of these pathways as critical resistance mechanisms in GBM, but also highlight novel strategies to antagonize these pathways to enhance therapeutic gain of radiation and temozolomide in GBM.

Inventors have demonstrated that the PI3K signaling pathway can be analyzed in glioblastoma patient biopsies using immunohistochemical analysis (in particular quantitative IHC, particularly AQUA® analysis) with activation-specific antibodies.

Significant biomarkers for Gefitinib-treated GBM patients (RTOG 0211) differs from that of historical, RT and non-Gefitinib-treated GBM patients. In Gefitinib-treated patients, those with higher levels of nuclear pAKT driven by PTEN loss, higher levels of nuclear pMAPK, and lower levels of nuclear pmTOR had significantly worse clinical outcomes. In contrast, in non-Gefitinib-treated patients, patients with PTEN-deficiency, and higher levels of EGFRvIII, total EGFR, IGFR1, NFkB and lower levels of nuclear Survivin appeared to have adverse clinical outcomes, highlighting the treatment-dependency of these biomarkers. In the upfront setting, activation of AKT signaling appears to be associated with adverse outcome in Gefitinib-treated GBM patients.

The examples below are illustrative and do not limit the invention to any specific embodiment.

EXAMPLES

Example 1

RTOG Study and AQUA® Analysis

This correlative biology study investigated how activation patterns of key signal transduction pathways correlate with clinical outcome in GBM patients treated by RT in the pre-temozolomide era using RTOG biorepository specimens. Tissue microarrays (TMAs) from 120+ GBM patients treated on historical RTOG studies have been generated. Using these RTOG TMAs, expression of twelve molecules from key signaling pathways including: EGFR, EGFRvIII, pAKT, pMAPK, PTEN, IGFR1, Src, pSrc, MGMT, Survivin, NfkB, and pmTor have been quantitatively assessed using the HistoRx AQUA® platform. Array 8 was generated using samples from patients treated with RT alone. Array 19 was generated using samples from patients treated with RT and Geftinib.

The AQUA® platform represents a molecular microscopy-based approach to quantitatively assess expression levels of molecules of interest in formalin-fixed paraffin-embedded (FFPE) tissues. The advantages of this RTOG-based analyses over previously-reported analyses (which have often resulted in conflicting data) are the following: 1) Meticulous collection of tissues on well-controlled, prospective RTOG clinical studies 2) AQUA® technology which avoids use of conventional immunohistochemistry (IHC) brown stain, which has been designed to see context rather than scoring intensity of expression 3) AQUA® technology which enables detection of molecules over a wider-range of expression versus traditional IHC 4) AQUA® technology which enables assessment of features based on molecular interactions rather than morphology-based. 5) AQUA® technology which is not biased by human selection for area used for staining as is the case for traditional IHC 6) AQUA® technology with the advantages of the accuracy and usage patterns of flow cytometry with retention of spatial and architectural information over IHC.

Staining Protocol

Paraffin sections were deparaffinized in xylene and hydrated and then put in Tris EDTA buffer PT Module™ Buffer 4 (100× Tris EDTA Buffer, pH 9.0) TA-050-PM4X (Lab Vision Corp, Fremont Calif.) for antigen retrieval. Sections were then rinsed once in 1×TBS Tween (Lab Vision, Fremont, Calif.) for 5 minutes and incubated in peroxidase block (Biocare Medical, Concord, Calif.) for 15 min followed by a rinse in 1×TBS Tween for 5 min. Sections were blocked using Background Sniper (Biocare Medical, Newport Beach, Calif.) for 15 min. Sections were incubated with the primary antibody cocktail, typically: rabbit anti-biomarker antibody and mouse anti-GFAP (DAKO, lot #M076101-2 at a 1:100 concentration) diluted in DaVinci Green (Biocare Medical, Newport Beach, Calif.) for 1 hours at room temp. Anti-biomarker antibodies used are shown in FIG. 1. Following three 5 min. rinses in 1×TBS Tween, slides were incubated in secondary antibody cocktail of goat anti-rabbit EnVision (DAKO, prepared per manufacturer's instructions) and goat anti-mouse Alexa Fluor 555 (Invitrogen A21429 diluted 1:200 into the EnVision) for 30 minutes in the dark, rinsed and then treated with Cy5 tyramide, diluted 1:50 in amplification buffer (Perkin Elmer SAT705A) for 10 min. room temperature in the dark, mounted with Prolong anti-fade with DAPI (Invitrogen, Carlsbad Calif.) and allowed to dry overnight.

Each stained specimen was imaged using a PM-2000™ system (HistoRx, New Haven Conn.) at 20× magnification. A board-certified pathologist reviewed an H&E stained serial section of the glioblastoma cohort to confine tumor tissue presence in the samples. Images were evaluated for quality prior to analysis as described in co-pending U.S. Application 60/954,303. AQUA® analysis of the biomarkers was conducted and the biomarkers are quantified within cytoplasmic and nuclear compartments as described in Camp et al 2002 Nature Medicine 8(11)1323-1327.

Cluster and Multivariate Analysis on the RTOG 0211 Specimens

AQUA® analysis generates a continuous score, from which analyses of relationship with patient outcome and/or disease treatment can be assessed. Differentiation of continuous AQUA® scores into clusters provides insight into subpopulations of patients. The first step is clustering using a cluster features tree and quick sequential clustering to form nodes of subjects (See, e.g., Zhang, T., R. Ramakrishnon, and M. Livny., An efficient data clustering method for very large databases. Proceedings of the ACM SIGMOD Conference on Management of Data, 1996). The second step is hierarchical agglomerative clustering with a Bayesian approach. This is an unsupervised method which allows the inclusion of both categorical and continuous data to build more complete clustering algorithms. This method allows for efficient handling of large datasets and that the Bayesian approach to determine number of clusters is reproducible and accurate. In addition, a supervised clustering method was utilized to further explore the datasets. Using both continuous and clustered (supervised or unsupervised) AQUA® scores, both a continuous Cox Proportional Hazard and a cluster based Kaplan-Meier (K-M) time to event analyses were conducted. Cox regression analyses with continuous AQUA® scores as covariates were conducted. Significance was computed as a change from the baseline model. In the K-M analyses, resulting survival curves were compared using the log-rank statistic.

Statistics

Outcome is defined as death due to disease or progression free time. Time was expressed in months from date of tumor collection to either death or censoring. Survival was expressed in mean or median survival (months). All AQUA® score distributions that were skewed required a log2 transformation to maintain normality. An unsupervised two step clustering algorithm was used to declare clusters based on the continuous AQUA® scores. The procedure was to first apply the BIRCH algorithm, a modified cluster feature (CF) tree method to form nodes of subjects (See, e.g., Zhang, T., R. Ramakrishnon, and M. Livny., An efficient data clustering method for very large databases. Proceedings of the ACM SIGMOD Conference on Management of Data, 1996). Secondly, these tree nodes were submitted to an agglomerative hierarchical clustering method. The numbers of final clusters were chosen in an unsupervised manner using the Schwartz's Bayesian Information criterion, where:

$$BIC = (-2 * \ln L + k \ln(n))$$

Successive models were compared and when there was a minimal change in BIC from the previous model, a final solution is declared. Statistics on critical points are determined by chi-square/t-tests and employ Bonferroni adjustments. Using existing clinical data, these clusters may be ascribed to certain subject groupings (i.e. groups of like ages, disease stage, gender, etc.). Where there were three or more clusters analyzed, further inspection of the survival curves was required to better define the relationship of subjects/clusters to outcome. Usually, only 1 additional look at the data was required with no penalty in p taken. In both Cox and K-M analyses, mean and when available, median time to event are reported for the full time array as well as smaller time periods depending on the array and disease investigated. In the multivariate Cox modeling, any biomarkers with a $p<0.2$ were included as potential contributors to the model, and the model was assessed over the full time period available for the cohort based on the followup information available.

Example 2

Analysis of Biomarkers in GMB Patients Treated with RT

Statistical analysis based on AQUA.RTM. scores showed that biomarkers EGFR, EGFRvIII, PTEN, IGFR1, Survivin and NfkB each were prognostic for GBM patients treated with radiation therapy alone. Higher PTEN nuclear scores indicated a better outcome and lower scores relatively worse outcome. Higher EGFRvIII non-nuclear scores indicated worse outcome and lower scores indicated relatively better outcome. Higher EGFR non nuclear scores indicated worse outcome and lower scores indicated relatively better outcome. Higher IGF-1R non nuclear scores indicated worse outcome, and lower scores indicated relatively better outcome. Higher NFkB non nuclear scores indicated worse outcome and lower scores indicated relatively better outcome.

Similar to that seen with HER2 expression (see McCabe et al 2005 J NCI 97(24)1808-1815), Survivin analysis was sensitive to titration of the antibody. At higher concentrations of anti-survivin antibody in the assay, low Survivin scores indicated worse outcome whereas higher scores indicated relatively better outcome. At lower concentrations of anti-survivin antibody in the assay, high survivin scores indicated worse outcome and lower scores indicated relatively better outcome.

Therefore a quantitative tissue-based assay for measuring biomarker levels in the context of tumor cells, and in some cases subcellular localization (i.e. nuclear or non-nuclear) is indicative of the relative prognosis of a patient suffering from glioblastoma (GBM), if they were to be treated with radiation therapy (RT) alone. Such an assay measuring at least one of the following markers is indicative of relative prognosis of a GBM patient if treated with RT: PTEN, EGFRvIII, EGFR, IGF-1R, NFkB (FIGS. 2-7, 9). If the assay results indicate a relatively high level of any of the following biomarkers, it is indicative of a relatively poor prognosis of a patient when treated with RT alone: EGFRvIII, EGFR, IGF-1R, NFkB (FIGS. 4-7, 9). If the assay results indicate a relatively low level of any of the following biomarkers, it is indicative of a relatively better prognosis of a patient when treated with RT alone: EGFRvIII, EGFR, IGF-1R, NFkB (FIGS. 4-7, 9).

If the assay results indicate a relatively low level of PTEN, it is indicative of a relatively poor prognosis of a patient when treated with RT alone (FIGS. 2, 3). If the assay results indicate a relatively high level of PTEN, it is indicative of a relatively better prognosis of a patient when treated with RT alone (FIGS. 2, 3).

Figure 8:
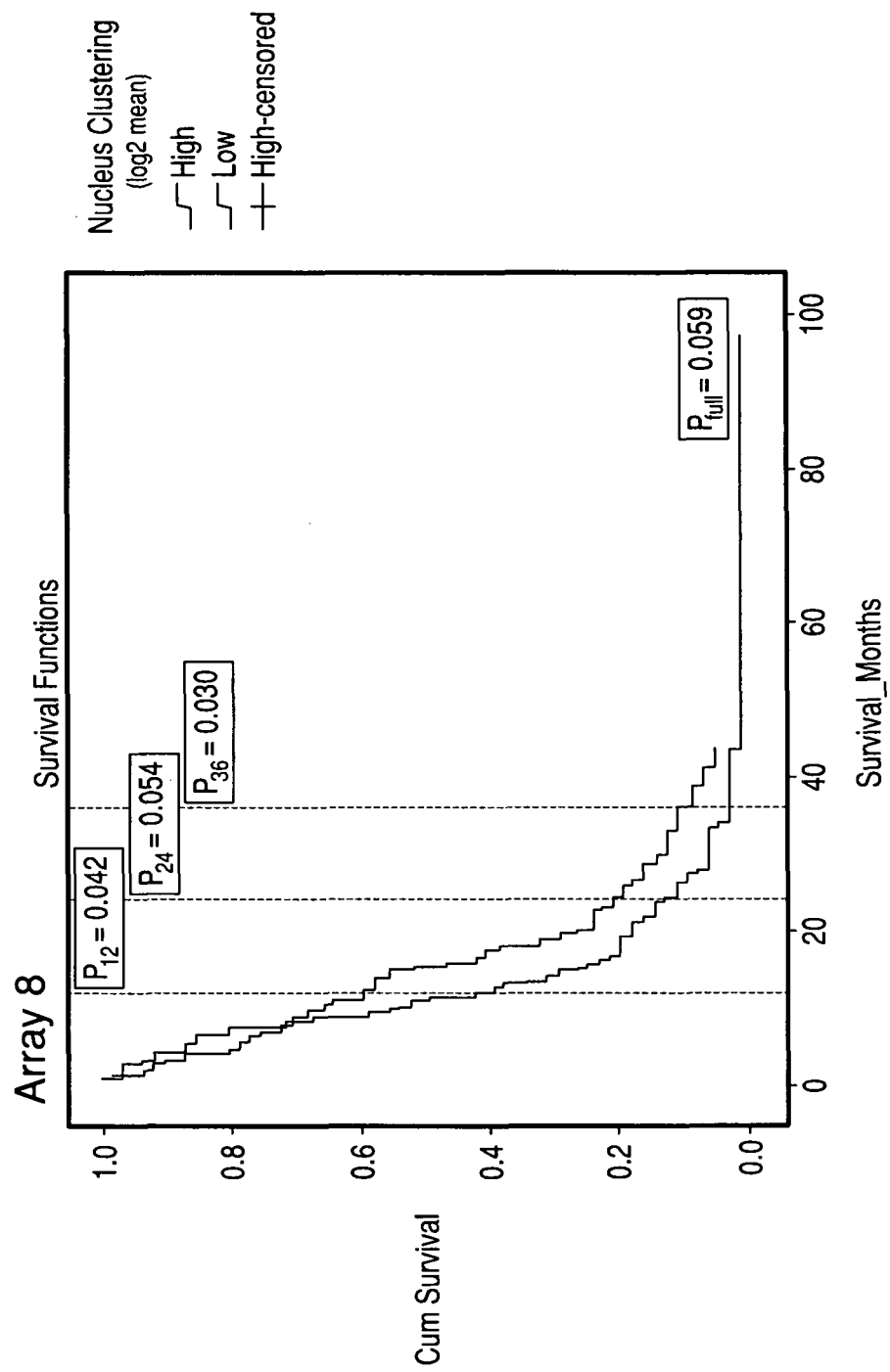
FIG. 8 is a Kaplan-Meier analysis of survival based on survivin scores from Array 8.
Figure 9:
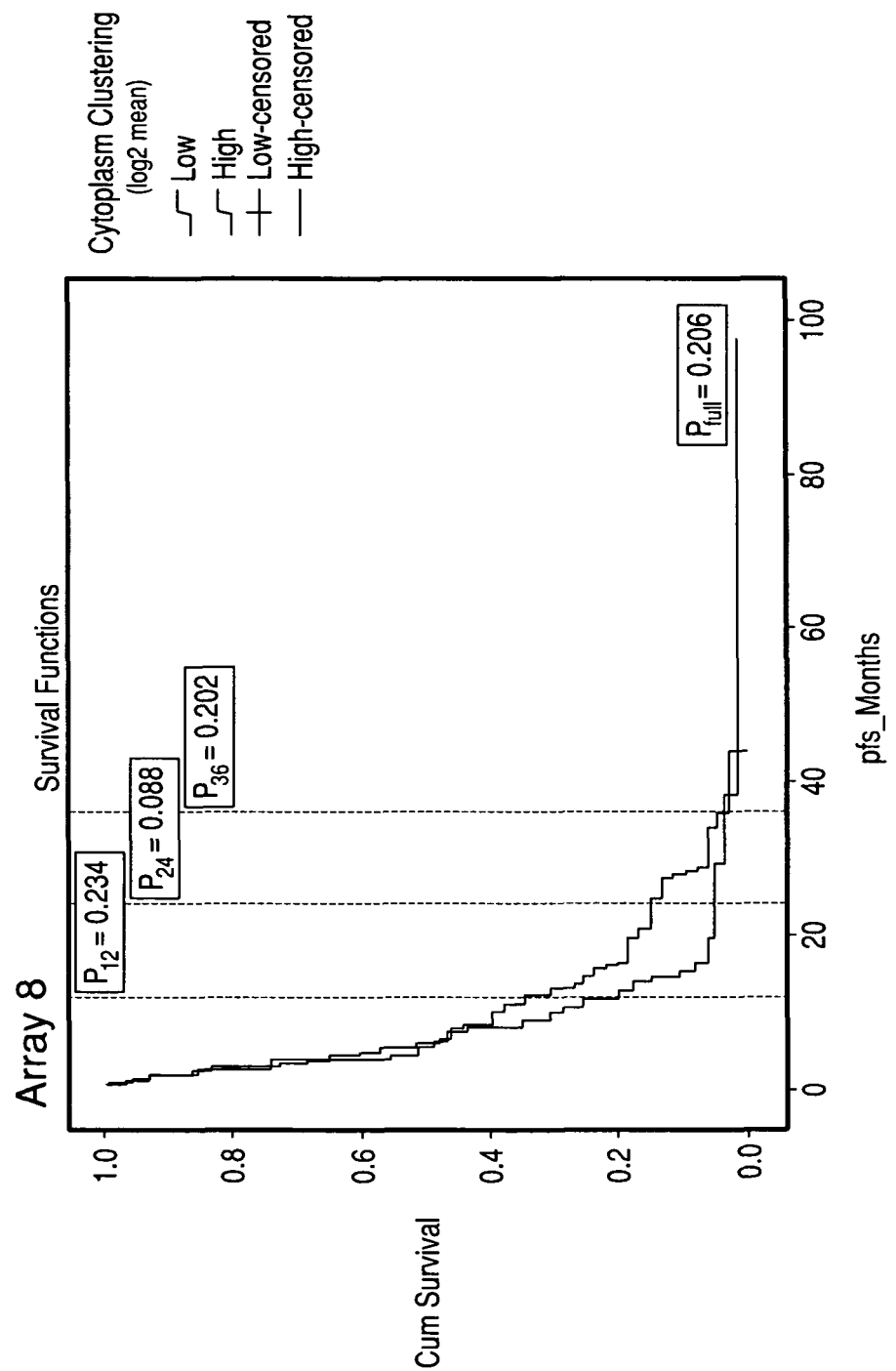
FIG. 9 is a Kaplan-Meier analysis of survival based on IGF-1R scores from Array 8.

An assay utilizing a low relative concentration of anti-survivin antibody for detection is indicative of a relatively poor prognosis for a patient treated with RT alone when the relative survivin score is high. An assay utilizing a low relative concentration of anti-survivin antibody for detection is indicative of a relatively better prognosis for a patient treated with RT alone when the relative survivin score is low. An assay utilizing a high relative concentration of anti-survivin antibody for detection is indicative of a relatively poor prognosis for a patient treated with RT alone when the relative survivin score is low. An assay utilizing a high relative concentration of anti-survivin antibody for detection is indicative of a relatively better prognosis for a patient treated with RT alone when the relative survivin score is high (FIG. 8).

Figure 14:
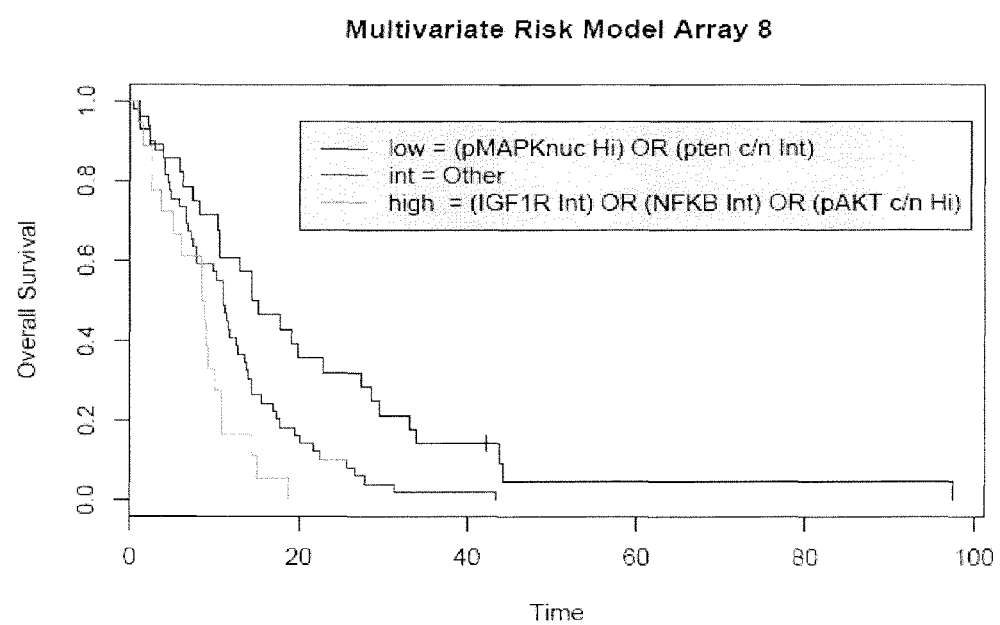
FIG. 14 is a multivariate risk model for overall survival based on biomarker scores from Array 8.

In a multivariate risk model for overall survival based on AQUA® scores for various biomarkers in Array 8 samples-patients treated with RT alone, significantly different overall survival was observed for each of three groups of patients. Poor prognosis was observed in patients with intermediate scores for IGF1R or NFkB or high cytoplasmic:nuclear ratio of pAKT. Relatively better prognosis was observed for patients with high nuclear pMAPK or intermediate cytoplasmic:nuclear PTEN ratio scores. (FIG. 14)

Figure 15:
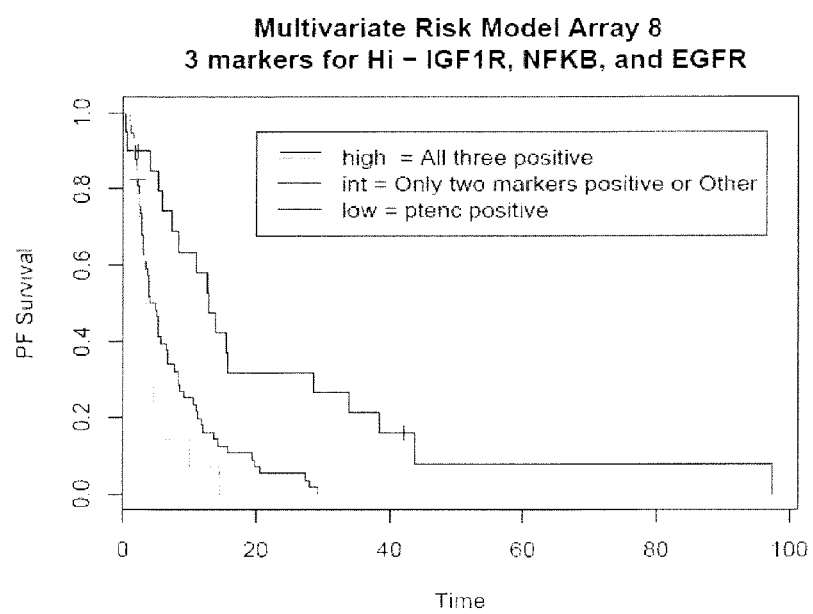
FIG. 15 is a multivariate progression free survival risk model based on biomarker scores from Array 8.

In a multivariate risk model of progression free survival based on AQUA® scores for various biomarkers in Array 8-patients treated with RT alone, significantly different PFS was observed for each of three groups of patients. Poorest PFS was observed in patients with high IGF1R, NFKB and EGFR. Patients with high PTEN scores were observed to have the best relative PFS. Patients with high levels of only two of the three markers, and remaining patients not falling into the previous two groups had an intermediate PFS. (FIG. 15)

Example 3

Analysis of Biomarkers in GBM Patients Treated with Gefitinib+RT

The RTOG conducted a Phase I/II clinical study of radiation with Gefitinib for 168 newly diagnosed GBM patients. Tissue was prospectively collected on 120 patients, making this the largest correlative analysis performed on Gefitinib-treated GBM patients. Interestingly, the significant biomarkers for Gefitinib-treated GBM patients on RTOG 0211 appeared to differ compared to historical, RT and non-Gefitinib-treated GBM patients (see above). Array 19 was generated using samples from these patients, which is described in Table 1 below.

TABLE 1

Patient population of samples on Array 19.

| Variables | Array 19 (N = 72) | Hazard Ratio | Lower95 | Upper95 | p-value |
|---|---|---|---|---|---|
| Diagnosis Age Continuous | | 1.0410 | 1.016 | 1.067 | 0.0013 |
| Diagnosis Age - Standardized by 10 | | 1.4942 | 1.170 | 1.908 | 0.0013 |
| Diagnosis Age Categorical | | | | | |
| <50 | 17 | 1.0000 | | | |
| [50, 60) | 23 | 1.3384 | 0.705 | 2.543 | 0.3733 |
| [60, 70) | 20 | 2.2388 | 1.146 | 4.373 | 0.0183 |
| 70+ | 12 | 4.2583 | 1.908 | 9.506 | 0.0004 |
| Gender | | | | | |
| Male | 43 | 1.0000 | | | |
| Female | 29 | 1.5122 | 0.921 | 2.484 | 0.1024 |
| Neuro Function | | | | | |
| 1 and 2 | 13 | 1.0000 | | | |
| 3 | 39 | 1.9196 | 0.972 | 3.792 | 0.0604 |
| 4 | 20 | 1.8816 | 0.892 | 3.971 | 0.0972 |
| Prior Surgery | | | | | |
| Partial Resection | 11 | 1.0000 | | | |
| Total Resection | 42 | 0.6174 | 0.309 | 1.233 | 0.1720 |
| 4 | 19 | 0.6403 | 0.297 | 1.379 | 0.2546 |

Figure 10:
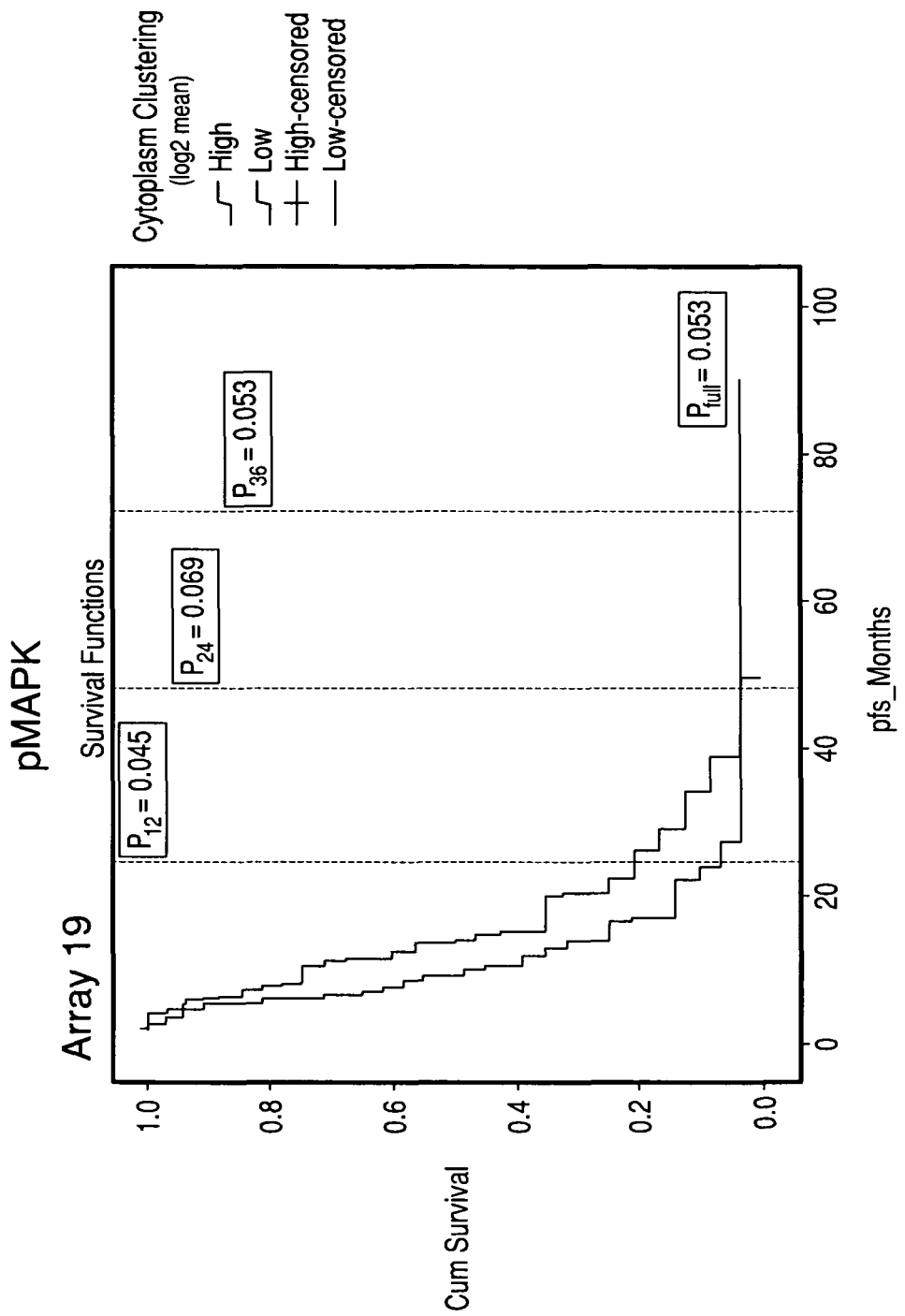
FIG. 10 is a Kaplan-Meier analysis of progression free survival based on pMAPK scores from Array 19.
Figure 11:
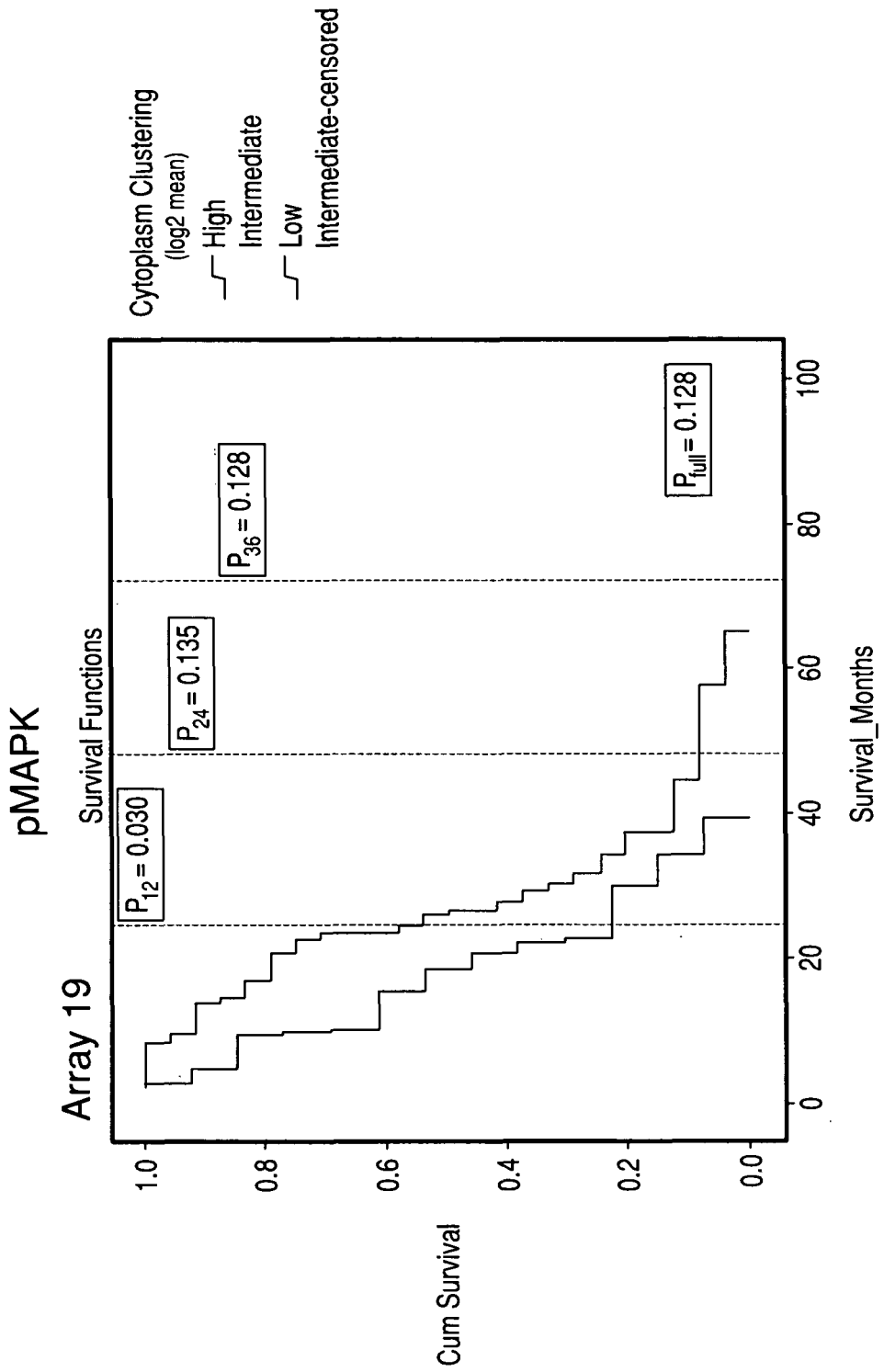
FIG. 11 is a Kaplan-Meier analysis of overall survival based on pMAPK scores from Array 19.
Figure 12:
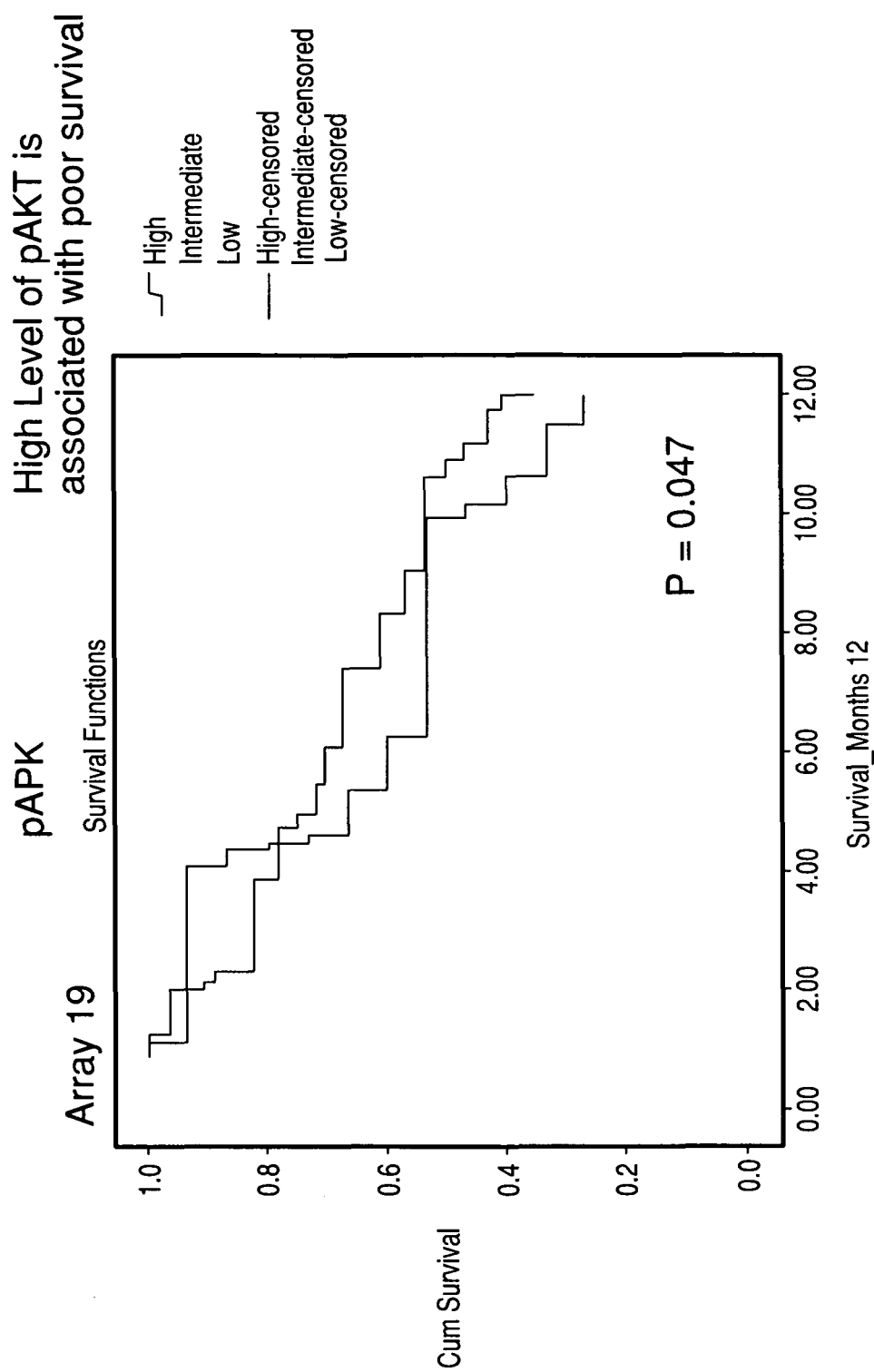
FIG. 12 is a Kaplan-Meier analysis of survival based on pAKT scores from Array 19.
Figure 13:
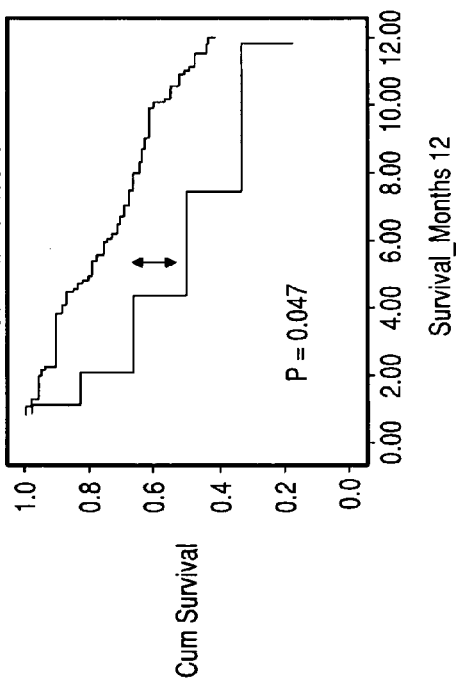
FIG. 13 is a multivariate model combining PTEN and AKT scores from Array 19.

In Gefitinib-treated patients, those with higher levels of nuclear pAKT driven by PTEN loss, higher levels of nuclear pMAPK, and lower levels of nuclear pmTOR had significantly worse clinical outcomes. In contrast, in non-Gefitinib-treated patients, patients with PTEN-deficiency, and higher levels of EGFRvIII, total EGFR, IGFR1, NFkB and lower levels of nuclear Survivin appeared to have adverse clinical outcomes, highlighting the treatment-dependency of these biomarkers, More specifically, statistical analysis based on AQUA.RTM. scores showed that biomarkers pAKT, pMAPK and pmTOR each were prognostic for GBM patients treated with radiation combined with gefitinib therapy. Higher pAKT nuclear scores indicated worse outcome and lower scores relatively better outcome. Higher nuclear pMAPK scores indicated worse outcome and lower scores indicated relatively better outcome. Higher non-nuclear pMAPK scores however, indicated better outcome whereas and lower scores indicated relatively worse outcome. Higher nuclear pmTOR scores indicated relatively better outcome whereas lower nuclear pmTOR scores indicated relatively poorer outcome. Therefore a quantitative tissue-based assay for measuring biomarker levels in the context of tumor cells, and in some cases subcellular localization (i.e., nuclear or non-nuclear) is indicative of the relative prognosis of a patient suffering from glioblastoma (GBM), if they were to be treated with radiation therapy (RT) combined with gefitinib. Such an assay measuring at least one of the following markers is indicative of relative prognosis of a GBM patient if treated with RT combined with gefitinib: pAKT, pMAPK (FIGS. 10-12). If the assay results indicate a relatively high level of pAKT and/or pMAPK biomarkers in the tumor cell nucleus, it is indicative of a relatively poor prognosis of a patient when treated with RT combined with gefitinib. If the assay results indicate a relatively low level of pAKT and/or pMAPK biomarkers in tumor cell nuclei, it is indicative of a relatively better prognosis of a patient when treated with RT combined with gefitinib. If the assay results indicate a relatively low level of pMAPK in tumor cell non-nuclear compartment, it is indicative of a relatively poor prognosis of a patient when treated with RT combined with gefitinib. If the assay results indicate a relatively high level of pMAPK in tumor cell non-nuclear compartment, it is indicative of a relatively better prognosis of a patient when treated with RT combined with gefitinib. See, FIGS, 10-12.

Figure 16:
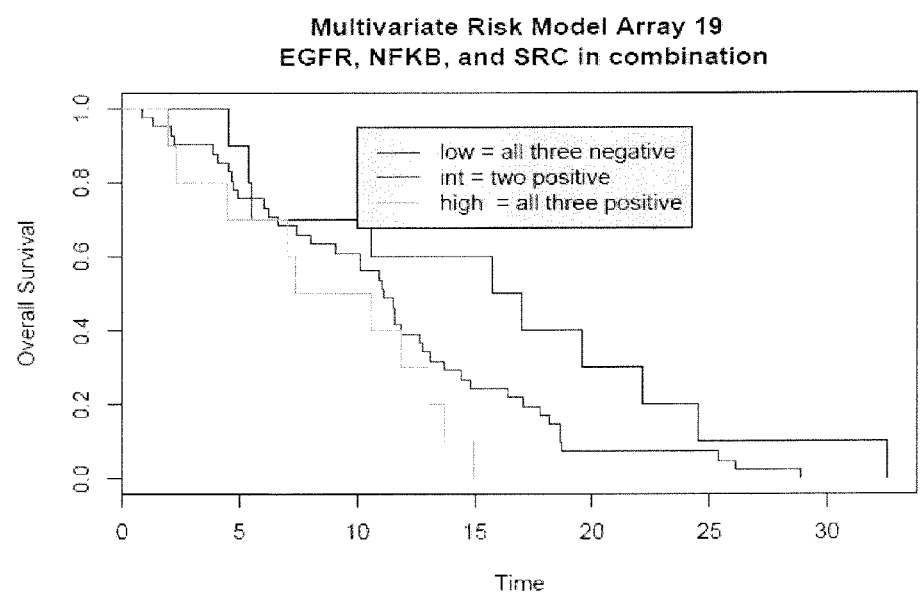
FIG. 16 is a multivariate risk model for overall survival based on biomarker scores from Array 19.

In a multivariate risk model assessment of Array 19 results, significantly different overall survival rates were seen for each of three groups of patients. Those with intermediate EGFR scores, high NFKB scores and intermediate and high SRC scores, were observed to have worse prognosis. Patients with the low and high extremes in EGFR scores, low SRC scores and low to intermediate NFKB scores had relatively better prognosis. All other patients had an overall survival prognosis falling intermediate of the previously described two groups. (See FIG. 16).

Figure 17:
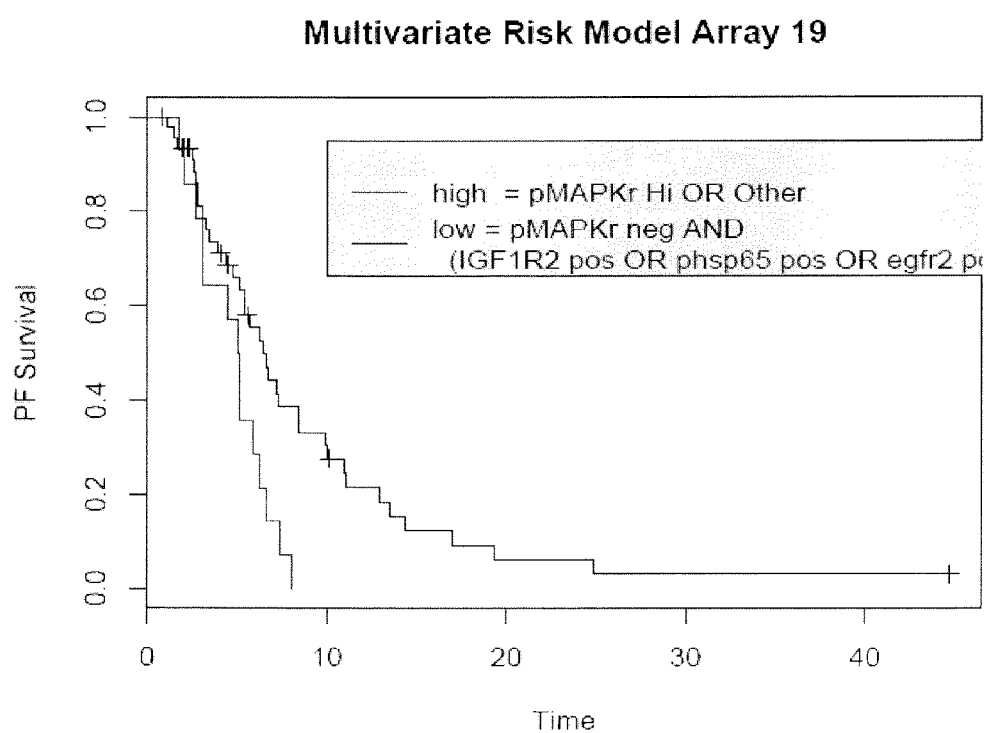
FIG. 17 is a multivariate risk model for progression free survival based on biomarker scores from Array 19.

In a multivariate risk model assessment of Array 19 results, significantly different progression free survival rates were seen for each of two groups of patients. Those with low pMAPK scores and (positive IGF-1R or p65 or EGFR) had relatively better progression free survival whereas all others had relatively poor progression free survival. (See FIG. 17).

Example 4

Univariate Analysis of GBM Patients

In addition to multivariate analysis, AQUA® analysis can be used to determine the prognostic value of individual biomarkers. Using the same Array 8 and Array 19 described above, the following individual biomarkers were analyzed. These biomarkers are associated with the EGFR pathway, and therefore can be used to identify those patients for whom EGFR-targeted treatments may be desirable. These data are in addition to and confirm the individual results of the multivariate data described above.

PTEN

In patients treated by RT alone, lower levels of PTEN, both nuclear as well as cytoplasmic, were associated with adverse overall survival, even when taking into factor significant clinical prognostic variables (age). When comparing clinical outcomes in patients with lower levels of PTEN expression stratified by treatment (RT alone versus RT+Gefitinib), there appears to be a trend towards improved outcome in patients treated by combined RT+Gefitinib (p=0.08).

pAKT

Patients treated by RT alone with elevated cytoplasmic to nuclear ratios of pAKT appeared to have significantly reduced survival times compared with patients with lower ratios within the same treatment group. When comparing clinical outcomes of patients with an elevated ratio of cytoplasmic to nuclear pAKT treated on RTOG 0211 with historical controls (patients treated by RT alone) with similar profiles, it becomes apparent that the addition of Gefitinib appears to be associated with improved overall survival in the Gefitinib-treated group.

Src

Patients with intermediate to high levels of Src demonstrated no differences in clinical outcomes compared to patients with low levels of Src among patients treated by RT alone. However, among patients treated with Gefitinb+RT (RTOG 0211), patients with intermediate to high levels of Src appeared to have significantly worse clinical outcomes compared to those with low expressions of Src. When comparing clinical outcomes of Geftinib+RT patients versus RT only patients stratified by intermediate-to-high levels of Src expression, it appears that Gefitinib-treated patients on RTOG 0211 actually had significantly worse overall survival times compared to patients treated by RT alone. This suggests that there may be molecular subgroups of patients who may actually fare worse with the addition of targeted agents such as Gefitinib.

IGFR1

For GBM patients treated with Gefitinib+RT on RTOG 0211, those with higher expression levels of IGFR1 protein expression had significantly worse overall survival times compared to patients with lower levels of IGFR1 expression (p=0.03).

These results confirm the usefulness of AQUA® analysis for determining the prognostic value of biomarkers, both individually and collectively. This analysis may be used to determine which patients may be suitable for a particular treatment, such as a treatment that targets a particular pathway, such as the EGFR pathway as described above. Other pathways may also be investigated using the methods described herein.

What is claimed is:

1. A method of determining a prognosis of a patient harboring a glioblastoma multiforme (GBM) tumor comprising:
    assessing a subcellular concentration or a relative concentration of one or more protein biomarkers selected from a group consisting of PTEN and pMAPK in a tissue specimen comprising GBM cells obtained from a patient harboring a GBM tumor;
    classifying a patient having a high nuclear pMAPK or intermediate cytoplasm to nuclear PTEN ratio as having a good prognosis if the patient is treated with radiation therapy alone, and
    administering to the patient classified as having a good prognosis radiation therapy alone.

2. A method of determining a prognosis of a patient harboring a glioblastoma multiforme (GBM) tumor comprising:
    assessing a subcellular concentration or a relative concentration of two or more protein biomarkers selected from a group consisting of EGFR, Src and NFkB in a tissue specimen comprising GBM cells obtained from a patient harboring a GBM tumor;
    classifying a patient having an intermediate level of EGFR, high level of NFkB and/or intermediate to high Src level as having a poor prognosis if the patient is treated with radiation therapy combined with gefitinib, and
    withholding from the patient classified as having a poor prognosis the administration of radiation therapy in combination with gefitinib.

3. A method of determining a prognosis of a patient harboring glioblastoma multiforne (GBM) tumor comprising:
    assessing a subcellular concentration or a relative concentration of two or more protein biomarkers selected from a group consisting of EGFR, Src, and NFkB in a tissue specimen comprising GBM cells obtained from a patient harboring a GBM tumor;
    classifying a patient having a low EGFR level, low Src level and/or low to intermediate NFkB level as having a good prognosis if the patient is treated with radiation therapy combined with gefitinib; and
    administering to the patient classified as having a good prognosis radiation therapy in combination with gefitinib.

4. A method of determining prognosis or relative survival risk of a patient harboring a glioblastoma multiforme (GBM) tumor if the patient is treated with radiation therapy combined with gefitinib comprising:
    assessing a concentration or a relative concentration of two or more biomarkers selected from a group consisting of EGFR, NFkB and Src in a tissue specimen comprising GBM cells obtained from a patient harboring a GBM tumor;
    classifying a patient with a positive expression of all biomarkers as having a poor prognosis for survival; no expression of all biomarkers as having a good prognosis for survival; and positive expression of any two biomarkers as having a relatively moderate prognosis for survival, and
    administering to the patient classified as having a good or moderate prognosis radiation therapy in combination with gefitinib.

* * * * *